US00PP20637P3

(12) United States Plant Patent
Huang

(10) Patent No.: US PP20,637 P3
(45) Date of Patent: Jan. 12, 2010

(54) ***DORITAENOPSIS* PLANT NAMED 'MOON N12'**

(50) Latin Name: *Doritaenopsis* sp.
Varietal Denomination: Moon N12

(75) Inventor: Tsung-Te Huang, Xinying (TW)

(73) Assignee: Tai-Ling Biotech Inc., Shinying, Tainan County (TW)

( * ) Notice: Subject to any disclaimer, the term of this patent is extended or adjusted under 35 U.S.C. 154(b) by 0 days.

(21) Appl. No.: 11/979,057

(22) Filed: Oct. 30, 2007

(65) Prior Publication Data

US 2009/0113585 P1 Apr. 30, 2009

(51) Int. Cl.
*A01H 5/00* (2006.01)

(52) U.S. Cl. ..... Plt./311

(58) Field of Classification Search ..... Plt./311
See application file for complete search history.

*Primary Examiner*—Kent L Bell
(74) *Attorney, Agent, or Firm*—Muncy, Geissler, Olds & Lowe, PLLC

(57) ABSTRACT

A new and distinct cultivar of *Doritaenopsis* plant named 'Moon N12' has white petals and sepals with light purple shadow near the labellum, upright and sturdy flowering stems, and excellent postproduction longevity.

2 Drawing Sheets

Botanical classification: *Doritaenopsis* sp.

Variety denomination: 'Moon N12'.

The present invention relates to botanical classification/cultivar designation: *Doritaenopsis* Orchid cultivar Moon N12.

BACKGROUND OF THE INVENTION

The present invention comprises a new and distinct cultivar of *Doritaenopsis* Orchid, and hereinafter is referred to by the cultivar name, 'Moon N12'.

The new cultivar is a planned breeding program conducted by the inventor in Tainan, Taiwan. The objective of the breeding program is to create new uniform pot-type *Doritaenopsis* Orchid cultivars having attractive flower coloration.

The new cultivar was discovered by the inventor from within the progeny of a cross-pollination of two unnamed proprietary selections of *Doritaenopsis* and *Phalaenopsis* Orchids, not patented, on Oct. 18, 1999, in a controlled environment in Tainan, Taiwan.

Asexual propagation by tissue culture in a laboratory in Tainan, Taiwan has been used to increase the number of plants for evaluation and has demonstrated that the unique combination of characteristics as herein disclosed for the new *Doritaenopsis* Orchid, 'Moon N12,' are retained through successive generations of asexual reproduction.

SUMMARY OF THE INVENTION

The following traits have been repeatedly observed and are determined to be basic characteristics of a new cultivar which, in combination, distinguish this *Doritaenopsis* Orchid as a new and distinct cultivar:

1. Flowers whose width in front view is broad, about 11 to 13 cm.
2. Flowers having a persistent habit.
3. Upright, freely branching and sturdy flowering stems.
4. Excellent postproduction longevity.

Plants of the new cultivar differ primarily from plants of the parent cultivar in flower color.

Plants of the new *Doritaenopsis* Orchid can be compared to plants of the male parent *Phalaenopsis* and the female parent *Doritaenopsis*. In side-by-side comparisons conducted in Tainan, Taiwan, plants of the new *Doritaenopsis* Orchid differed from plants of the male parent *Phalaenopsis* and the female parent *Doritaenopsis* in the following characteristics:

1. Plants of the new *Doritaenopsis* Orchid are bigger than plants of the male parent *Phalaenopsis* and the female parent *Doritaenopsis*.
2. Plants of the new *Doritaenopsis* Orchid have broader leaves than plants of the male parent *Phalaenopsis* and the female parent *Doritaenopsis*.
3. Plants of the new *Doritaenopsis* Orchid have shorter inflorescences than plants of the male parent *Phalaenopsis* and the female parent *Doritaenopsis*.

Plants of the new *Doritaenopsis* Orchid have stronger peduncles than plants of the male parent *Phalaenopsis* and the female parent *Doritaenopsis*.

BRIEF DESCRIPTION OF THE DRAWINGS

Colors in the photographs may appear different from the color values that appear in the detailed botanical description which accurately describe the new cultivar.

DETAILED DESCRIPTION OF THE PREFERRED EMBODIMENTS

Figure 1:
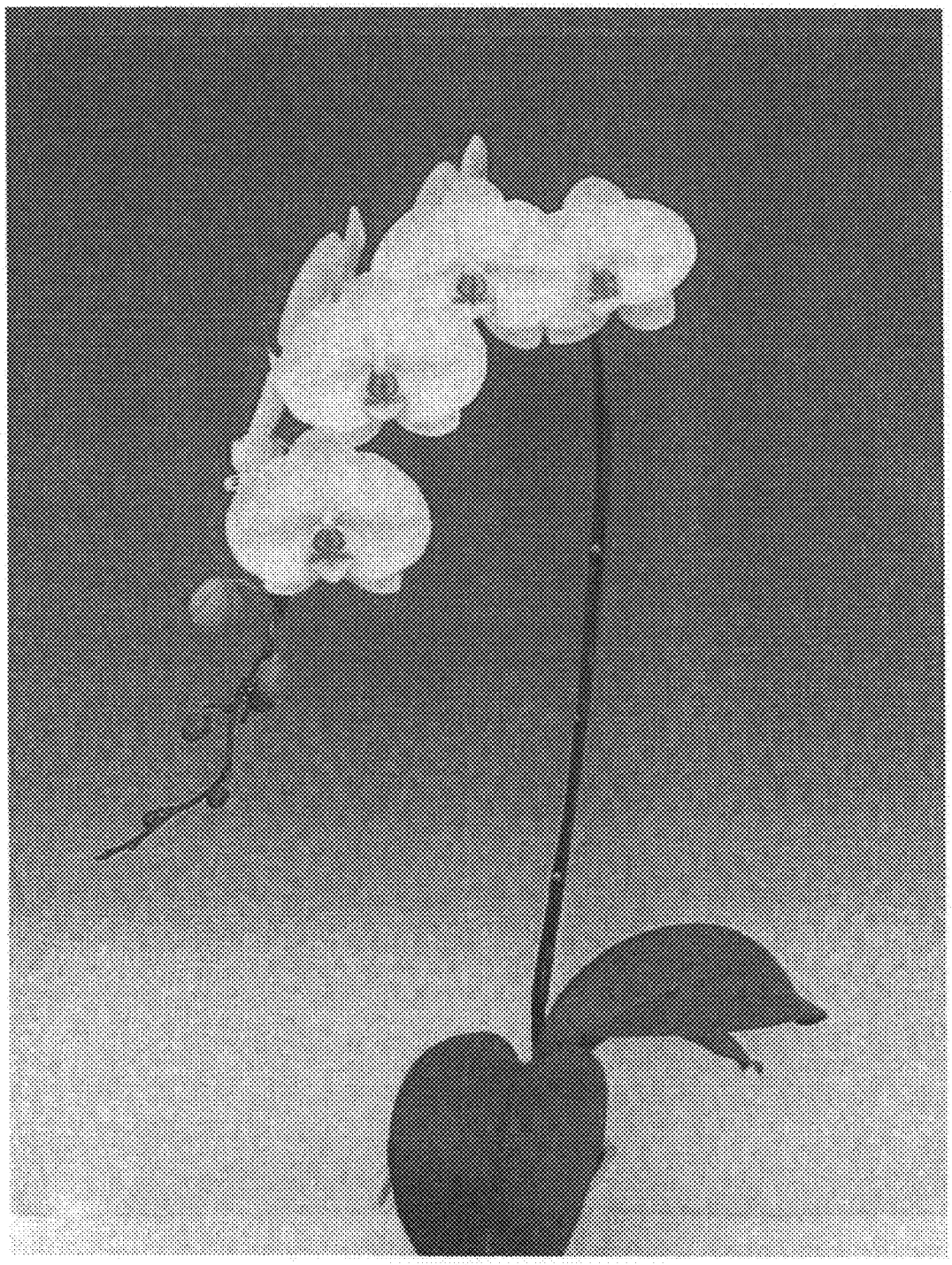
FIG. 1 is a side view of a plant of 'Moon N12' flowering in a 12 cm pot.
Figure 2:
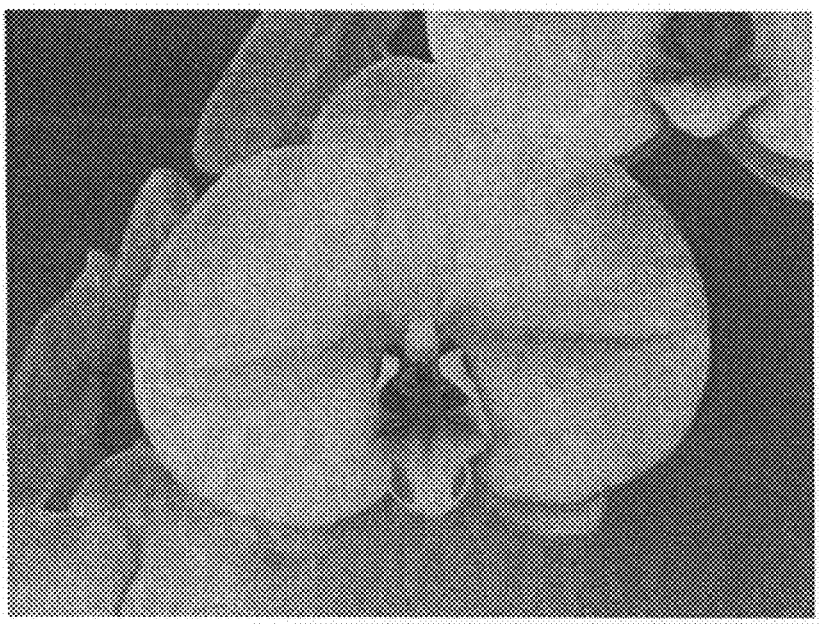
FIG. 2 is a close-up view showing the characteristics of the flower.
Figure 3:
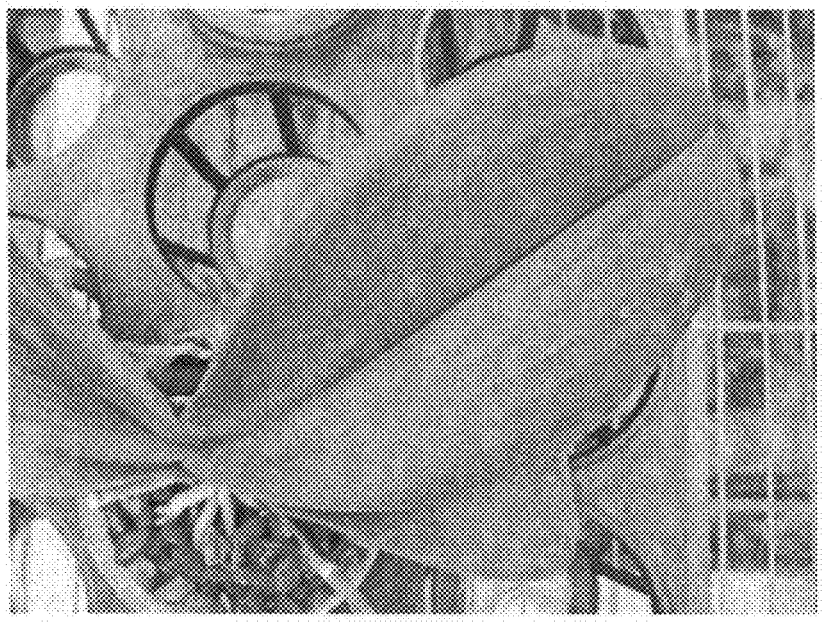
FIG. 3 is a close-up view showing the characteristics of the leaf.

Plants of the new cultivar have not been observed under all possible environmental conditions. The phenotype may vary significantly with variations in environment such as temperature and light intensity, without however, any change in genotype. In the following description, color references are made to The Royal Horticultural Society Colour Chart, except where general terms of ordinary dictionary significance are used.

Parentage:

*Seed.*—Unnamed proprietary selection of *Doritaenopsis,* not patented.

*Pollen.*—Unnamed proprietary selection of *Phalaenopsis,* not patented.

*Propagation.*—Asexual propagation by tissue culture.

Plant description:

*Plant shape.*—Two-ranked leaves affixed to a short central stem (monopodial growth). Single flowers are arranged on upright and sturdy flowering compound racemes.

*Plant height, soil level to top of foliar plane.*—About 15 to 20 cm.

*Plant height, soil level to top of inflorescences.*—About 90 to 95 cm.

*Distance from first flower to last flower per stem.*—Approximately 40 to 45 cm.

*Plant diameter.*—About 35 to 40 cm.

Foliage description:

*Quantity per plant.*—About 5 to 6.

*Length.*—About 23 to 24 cm.

*Width.*—About 9 to 10 cm.

*Shape.*—Obovate.

*Apex.*—Obtuse and rounded to retuse.

*Base.*—Cuneate.

*Margin.*—Entire.

*Aspect.*—Mostly flat and folded upward form the midrib.

*Texture, upper and lower surfaces.*—Leathery, thick, glabrous.

*Venation.*—Parallel; veins are sunken within the lamina.

*Color* (*upper surface*).—Closest to RHS 137A.

*Color* (*lower surface*).—Closest to RHS 146B.

Flower description:

*Flower type.*—Single zygomorphic flowers, roughly elliptical in shape.

*Flower arrangement.*—Racemes.

*Flowering stems.*—Upright.

*Flowering habit.*—Plants typically produce one to two branched flowering stems with at least 10 to 11 flowers each.

*Fragrance.*—Flowers are not fragrant.

*Self cleaning or persistent.*—Flowers persistent.

*Natural flowering season.*—From January to May in southern Taiwan.

*Post-production longevity.*—Plants of 'Moon N12' maintain good leaf and flower substance for about four to five months on the plant under interior environmental conditions.

*Inflorescence length.*—About 42 to 45 cm.

*Inflorescence diameter.*—About 38 to 40 cm.

*Flower diameter.*—About 11 to 11.5 cm.

*Flower depth.*—About 9 cm.

Petals:

*Quantity.*—Two per flower.

*Length.*—About 7.5 cm.

*Diameter.*—About 5.5 cm.

*Shape.*—Broadly ovate.

*Apex.*—Rounded.

*Base.*—Chunky, fused with the column.

*Margin.*—Entire.

*Texture, upper and lower surfaces.*—Velvety, smooth.

*Color.*—The main color of both the adaxial and abaxial surfaces of the petal is RHS 155B. The adaxial surface has a pattern color of RHS 76A, and the abaxial surface has a pattern color of RHS 74D.

Labellum:

*Width, not flattened.*—About 2 cm.

*Length, not flattened.*—About 2.3 cm.

*Callosites.*—Present.

*Shape.*—Deeply three-lobed with two prominent callosities on the upper surface at the central junction of the lateral lobe and base of midlobe.

*Base color of the upper and lower surfaces of the apical lobe.*—RHS 185B.

*Tip color of the upper and lower surfaces of the apical lobe.*—RHS N155B.

*Color of the callosities.*—RHS 7A.

Sepals:

*Quantity.*—Three per flower.

*Length.*—About 5.5 cm.

*Diameter.*—About 4.3 cm.

*Shape.*—Elliptic to ovate.

*Apex.*—Rounded.

*Base.*—Attenuate; fused with the petals and column.

*Margin.*—Entire.

*Texture, upper and lower surfaces.*—Velvety; smooth.

*Dorsal sepal main color.*—RHS N155B.

*Dorsal sepal pattern color.*—RHS 76B.

*Lateral sepal main color* (*upper surface*).—RHS N155B.

*Laterial sepal main color* (*lower surface*).—RHS 76B.

*Lateral sepal pattern color* (*upper surface*).—RHS 71A.

*Lateral sepal pattern color* (*lower surface*).—RHS 76B.

Peduncles:

*Length.*—About 50 to 55 cm.

*Diameter.*—About 5 mm.

*Aspect.*—Upright.

*Strength.*—Strong, sturdy.

*Texture.*—Smooth, glabrous.

*Color.*—RHS 200D.

Pedicels:

*Length.*—About 4 cm.

*Diameter.*—About 9 mm.

*Aspect.*—About 75° from vertical.

*Strength.*—Strong.

*Texture.*—Smooth, glabrous.

*Color.*—RHS 137A.

Reproductive organs: The stamens and pistils are fused into a column, and anthers with pollen grains are united into a pollinia. The stigma is situated under the column and behind the pollinia.

*Column.*—Length: About 1.2 cm. Diameter: About 5 mm. Color: RHS 75D.

*Pollinia.*—Quantity: Two. Diameter: About 1 mm. Color: RHS N25A.

*Ovary.*—Length: About 8 mm. Diameter: About 2.5 mm. Color: RHS 76D.

Root: In summer and winter, it took about 50 days at 27° C. to initiate and elongate roots. In summer, it took about 176 days at 27° C. to produce a fully rooted young plant. In winter, it took about 192 days at 27° C. to produce a fully rooted young plant.

*Diameter.*—About 4.5 mm.

*Color.*—RHS 144A.

Plant disease resistance/susceptibility: Resistance to known pathogens and pests common to *Doritaenopsis* Orchids has not been observed on plants of the new cultivar grown under commercial greenhouse conditions.

Temperature tolerance: Plants of the new *Doritaenopsis* Orchid have been observed to be tolerant to temperatures from about 15 to 32° C.

What is claimed is:

1. A new and distinct cultivar of *Doritaenopsis* plant named 'Moon N12', as illustrated and described.

* * * * *